United States Patent
Messler

(10) Patent No.: US 7,268,866 B2
(45) Date of Patent: Sep. 11, 2007

(54) METHOD FOR INSPECTING A WELD SEAM IN A WORKPIECE MADE OF WELDABLE PLASTIC AND DEVICE FOR CARRYING OUT THIS METHOD

(75) Inventor: Andreas Messler, Heiligenhaus (DE)

(73) Assignee: Huf Tools GmbH, Velbert (DE)

( * ) Notice: Subject to any disclaimer, the term of this patent is extended or adjusted under 35 U.S.C. 154(b) by 323 days.

(21) Appl. No.: 10/475,500

(22) PCT Filed: Apr. 5, 2002

(86) PCT No.: PCT/EP02/03789

§ 371 (c)(1),
(2), (4) Date: Oct. 22, 2003

(87) PCT Pub. No.: WO02/090953

PCT Pub. Date: Nov. 14, 2002

(65) Prior Publication Data

US 2004/0114662 A1    Jun. 17, 2004

(30) Foreign Application Priority Data

May 5, 2001   (DE) ................................. 101 21 923
Nov. 27, 2001   (DE) ................................. 101 58 095

(51) Int. Cl.
*G01N 21/88* (2006.01)
(52) U.S. Cl. ................. 356/237.1; 356/239.1; 356/430
(58) Field of Classification Search ........ 356/429–431, 356/237.1, 239.1
See application file for complete search history.

(56) References Cited

U.S. PATENT DOCUMENTS

| 4,491,719 A | * | 1/1985 | Corby, Jr. ............... 219/124.34 |
| 5,071,180 A | * | 12/1991 | Wiedehage et al. ......... 292/268 |
| 5,260,766 A | * | 11/1993 | Armitage .................. 356/237.1 |

FOREIGN PATENT DOCUMENTS

| DE | 4311320 | | 10/1994 |
| DE | 19603675 A1 | * | 8/1997 |
| DE | 297 07 777 U1 | | 10/1997 |
| DE | 29816401 U1 | * | 1/1999 |
| FR | 2369560 | | 5/1978 |
| JP | 10100259 A | * | 4/1998 |

OTHER PUBLICATIONS

Patent Abstracts of Japan, vol. 1998, No. 09, Jul. 31, 1998 & JP 10 100259 A (Nannichi Yasuo; Sekisui Chem Co Ltd), Apr. 21, 1998.

* cited by examiner

*Primary Examiner*—Richard A. Rosenberger
(74) *Attorney, Agent, or Firm*—Friedrich Kueffner

(57) ABSTRACT

The invention relates to an inspection method for inspecting the quality of a weld seam (15) during which a material, which is transparent to electromagnetic radiation (30) of a defined frequency, is used in a workpiece (10) consisting of two plastic parts (11, 12). In order to be able to reliably inspect the weld seam, the invention provides that an electromagnetic inspection radiation (30) is irradiated inside the workpiece (10). The resulting reflections between the boundary surfaces in the workpiece (10) and the portions of inspection radiation (30, 30') exiting from the workpiece (10) are affected by the quality of the produced weld seam (15). (15). By measuring the exiting radiation (33, 33'), it can be clearly determined whether the workpiece (10) has a defective or a tolerable seam (15).

7 Claims, 4 Drawing Sheets

1

METHOD FOR INSPECTING A WELD SEAM IN A WORKPIECE MADE OF WELDABLE PLASTIC AND DEVICE FOR CARRYING OUT THIS METHOD

BACKGROUND OF THE INVENTION

1. Field of the Invention

The invention concerns a method for inspecting a weld seam. The weld seam between the two materials is produced by a laser beam One of the plastic materials of which the workpiece is made is essentially transparent to this laser radiation, whereas the other plastic material absorbs the laser radiation.

2. Description of the Related Art

In the previously known method of this type, the inspection was performed with a pyrometer, which responds to the thermal radiation emitted by the weld seam that has been produced. For the pyrometer to reach the highest possible temperature, the measurement must be made during welding. In addition, the material of which one of the plastic parts is made must be capable of transmitting thermal radiation.

Laser radiation has proven to be very effective for welding plastics. There are three welding methods for laser radiation, namely, "track welding", "simultaneous welding", and "quasi-simultaneous welding". Pyrometric inspection of the weld seam is possible only with track welding and cannot be used in simultaneous welding or quasi-simultaneous welding, although the latter provides a time advantage over track welding. In the case of a welded product produced by the simultaneous welding method, inspection of the welded materials could be made only indirectly, by dimensional changes in the workpiece and could only be used with certain workpiece geometries. The quality of a simultaneous weld or quasi-simultaneous weld generally could not be inspected.

The pyrometric weld inspection possible in the case of track welding is also subject to error and can be used only if the material of one of the plastic parts transmits not only laser radiation but also thermal radiation. Therefore, in many cases, weld inspection of the finished workpiece is not possible at all.

In one well-known method of a different type (DE 196 03 675 A1), the weld joint is produced by contact welding of two superimposed plastic sheets from which a bag is to be produced. Each of the two plastic sheets itself consists of two layers, namely, a transparent, infusible outer support layer and a colored inner sealing layer. The contacting sealing layers of the two sheets are welded together by two heated sealing jaws pressing against each other. As a result of the weld joint on the colored sealing layers, the transparency of the weld seams changes relative to places that were not welded or were not adequately welded. These transparency differences are determined by a light transmission method and used to inspect the quality of the weld joints. The two sheets are transilluminated in the region of the weld seam by a light source, and the light emerging at the other side of the sheet is detected by a sensor and analyzed. This well-known method cannot be applied to weld seams produced by laser radiation, because one of the plastic parts of this welded product is absorbent and therefore opaque.

In another method for inspecting weld seams in bags produced from two sheets, which are then to be immediately filled with some substance (U.S. Pat. No. 5,260,766 A), laser light is projected into a transparent heated seal bar through a large number of glass fibers. In this way, the light reaches the contact area between this heated seal bar and an opposing bar, between which the two sheets are positioned and sealed. The light reflected from this contact area must pass back through the transparent material of the heated seal bar to produce an image, which is picked up by a camera and analyzed to determine whether particles of the material used to fill the bag are enclosed in the weld seam. This makes it possible to determine the quality of the weld seam. This method can be used only with thin flat sheets in which linear weld seams are formed and requires a transparent welding tool. It cannot be applied to the laser welding of three-dimensional plastic parts with two-dimensional or three-dimensional weld seams, especially if two plastics with different optical and/or mechanical properties are to be welded together.

Furthermore, it is also well known (DE 298 16 401 U1) that a transillumination technique can be used to detect cracks in a welded lap joint produced by the lap welding of sheets. In this method, the weld seam is placed between an optical transmitter and an optical receiver. To increase the accuracy of the measurement, this transillumination technique is carried out in a liquid with an extremely low viscosity. This method is not suitable for the inspection of weld seams produced by laser radiation between two plastic parts, one of which is absorbent.

Finally, it is well known (JP 10[1998]-100,259 A, Patent Abstracts of Japan, Vol. 1998, No. 09, Jul. 31, 1998) that two similar polyethylene materials can be irradiated with broad-band infrared radiation. As long as the resulting weld seam is in the liquid state, the infrared radiation reflected by the liquid or passing through the liquid is optically detected and analyzed. A laser beam is not used. Inspection radiation is not used in addition to the infrared radiation, so it does not matter whether one of the polyethylene materials is transparent to inspection radiation.

SUMMARY OF THE INVENTION

The objective of the invention is to develop a reliable inspection method of the type specified above, which avoids the aforementioned disadvantages of the state of the art. In accordance with the invention, this objective is achieved by the measures specified below.

In the interior of the welded product, reflections of the inspection radiation occur at all material interfaces between the two plastic parts of the workpiece, and, in accordance with the invention, the reflections of the inspection radiation from the already solidified, finished weld seam are analyzed. If the welding seam should have an unintended gap where imperfect welding or no welding has taken place, the reflections emanating from this location are of course also detected and evaluated in the same manner. If the weld seam that has been produced is imperfect, the radiation emerging from the workpiece is significantly changed. The quality of the weld seam can be clearly determined in this way. An evaluation unit detects the inspection radiation emerging from the welded workpiece and triggers suitable reactions in a monitoring device in the event of problems with the measured inspection radiation due to an imperfect weld.

The invention proposes two different measures as inspection radiation, each of which has independent inventive significance. One possibility, in accordance with Claim 2, consists in using additional radiation, that is completely independent of the laser radiation, for the inspection. It is only necessary to select as the inspection radiation an electromagnetic frequency at which at least one of the two plastic parts is transparent to this inspection radiation. These measures can then be used not only during the welding operation itself, but also later on the finished welded product. This control method could also be used if the welding seam has not been produced by laser radiation, but in some other manner.

However it is especially advantageous to use the laser radiation used to produce the weld seam as the inspection radiation. The measurement then detects the radiation emanating from an already solidified area of the resulting weld seam. This is possible, because the laser radiation reaching the interior of the workpiece is scattered inside the workpiece, and by suitably offsetting the detector, the area that is detected is some distance from the focus of the laser beam. The laser radiation that has already been repeatedly scattered in the laser-welded workpiece is used for the inspection. In this way, one obtains results based on reflections after solidification of the weld seam. When an unsatisfactory result is obtained, the defective workpiece can be removed immediately.

Additional measures and advantages of the invention are apparent from the dependent claims, the following description, and the drawings. Several embodiments of the invention are illustrated in the drawings.

DETAILED DESCRIPTION OF THE INVENTION

Figure 1:
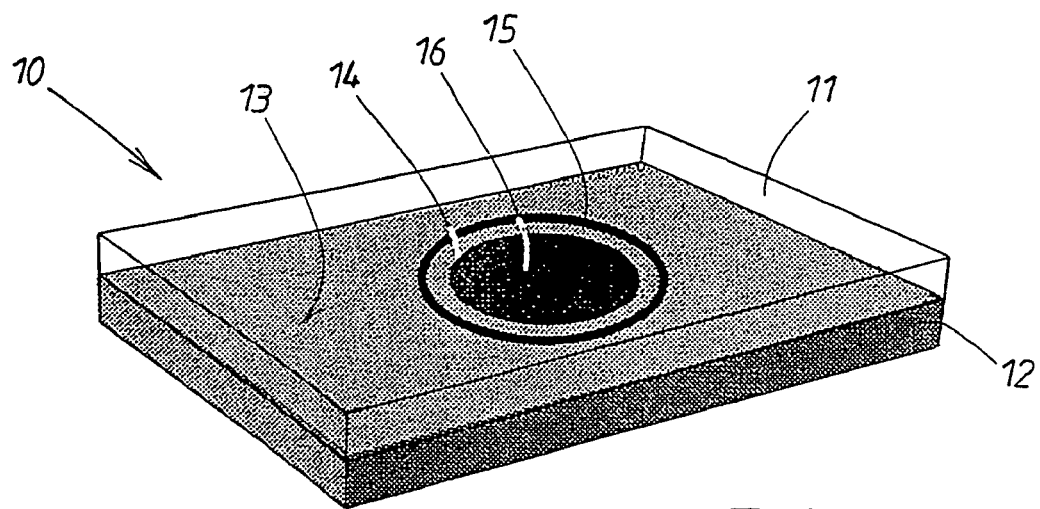
FIG. 1 is a schematic perspective view of an example of a welded product, namely, a transponder integrated in a two-layer workpiece.
Figure 2:
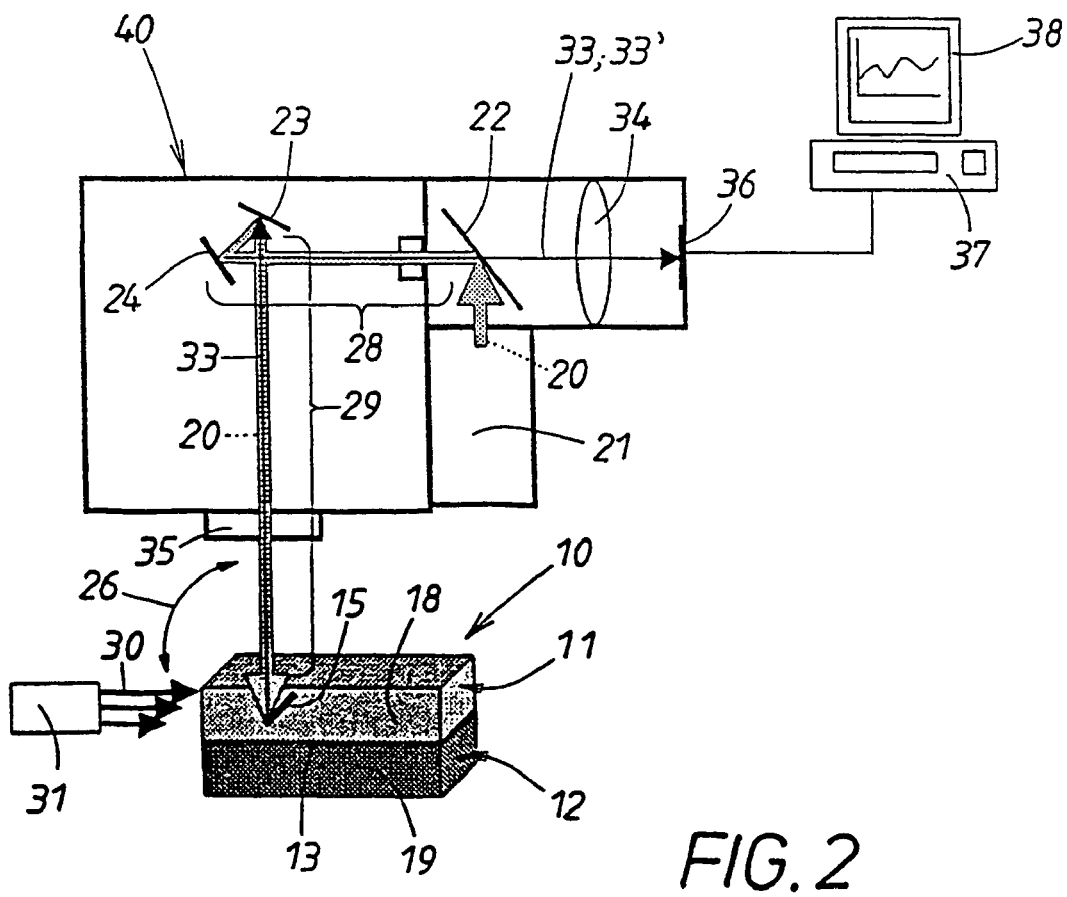
FIG. 2 shows a first, photometric method for inspecting the quality of the weld seam.

The workpiece 10 shown in FIG. 2 consists of two plate-like plastic parts 11, 12, which, at least in certain places between them, have a contact surface 13, on which a weld seam 15 is to be formed. An example of a finished welded product of this type is illustrated in FIG. 1.

For better recognition of the parts, the upper plastic part 11 is shown as transparent in FIG. 1 to allow a view of its contact surface 13 with the other plastic part 12 beneath it. The second plastic part 12 has a seat 14 for holding a plate-shaped transponder 16, which is able to receive, store, and transmit electronic data. A transponder of this type is temperature-sensitive and must be protected from environmental influences, such as moisture. The inserted transponder 16 is enclosed here by an annular weld seam 15, which joins the two layers of plastic 11, 12 in the area of the contact surface 13. This weld seam 15 provides media-tight enclosure of the transponder inside the workpiece 10.

Figure 4:
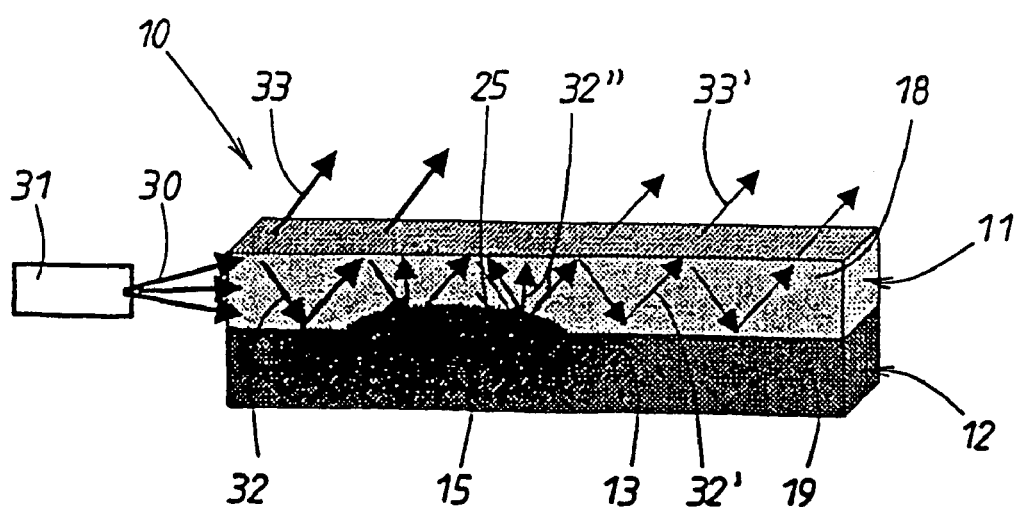
FIG. 4 shows, in a representation analogous to FIG. 3, the conditions that exist, when a weld seam has formed between the two plastic parts.

FIG. 2 shows a first method for both producing and inspecting a weld seam 15 of this type. This is accomplished with a combined device 40 for producing and directing a laser beam 20, which is shown as a shaded arrow. The laser beam is produced in a semiconductor laser module 21. The laser beam 20 strikes a deflecting mirror 22, which is transparent to another, especially electromagnetic, beam 30, whose formation will be described in greater detail below. As the beam path in FIG. 2 shows, the laser beam 20 strikes two movable beam-deflecting mirrors 23, 24. These two mirrors 23, 24 are moved in a well-defined way to direct the laser beam 20 to the workpiece 10 through a theta objective 35. With the two mirrors 23, 24, the weld seam 15 can be produced by the simultaneous welding method mentioned at the beginning, which can be carried out especially fast and inexpensively. The two plastic parts 11, 12 of the workpiece have the following properties in this case:

The material 18 of the first plastic part 11 is essentially transparent to the laser beam 20, but the material 19 of the second plastic part 12 absorbs the laser beam 20. The transparent plastic may consist of an amorphous material and thus cause little scattering. However, the plastic 18 may also be semicrystalline, i.e., it may have a large scattering effect. This causes liquefaction of the two plastic materials 18, 19 in some areas of the contact surface 13. The enlargement in FIG. 4 shows what happens in the workpiece 10. FIG. 4 shows the cross section of the resulting weld seam 15, which consists of a mixture of the two starting materials 18, 19. As FIG. 4 shows, compared to the original contact surface 13, another interface 25 forms relative to the two plastic materials 18, 19, which remain unmixed and enclose the interface 25.

Next to the workpiece 10, there is a source 31 for electromagnetic radiation 30, which is independent of the laser beam 20 and hereinafter will be referred to simply as "inspection radiation" for reasons that will become apparent. Used as the inspection radiation 30 may also be a laser radiation, but also another electromagnetic radiation, such as ultraviolet or infrared radiation, or also visible light. The selection is also in this case dependent on the materials used. As FIG. 2 illustrates, this inspection radiation 30 is introduced into the workpiece 10 at a suitable angle 26 to the laser beam 20 entering from the combination device 40. In the present case, the plastic material 18 of the upper layer 11 should also be transparent to the inspection radiation 30. What then happens is explained in greater detail below with reference to FIG. 3, on the one hand, and to FIG. 4, on the other hand.

Figure 3:
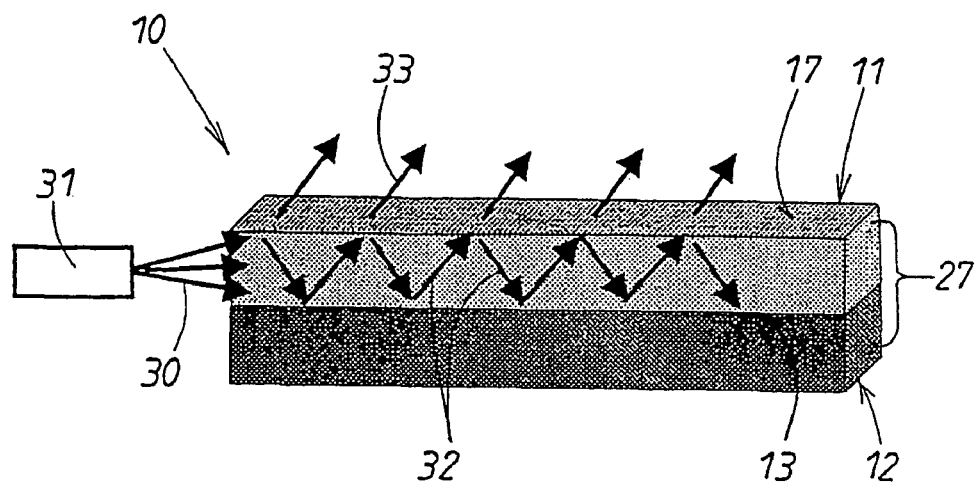
FIG. 3 shows the operating principle of the method used in FIG. 2, when there is no weld seam between the two plastic parts of the workpiece.

FIG. 3 shows the conditions in the workpiece 10, when, in the extreme case, no welding of the plastic parts 11, 12 occurs at their contact surface 13. In the interior 27 of the workpiece 10, the inspection radiation 30 experiences multiple reflections 32 between the contact surface 13 and the outer surface 17. A portion of the reflected radiation 32 striking the outer surface 17 exits, as the arrows 33 in FIG. 3 show, and is gathered by the theta objective 35 of the device 40 of FIG. 2. As FIG. 2 makes clear, this exiting inspection radiation 33 travels along the segments 28, 29 of the optical path in the device 40 that the laser beam 20 follows. However, due to the transparency of the deflecting mirror 22 to the inspection radiation, this radiation passes through the deflecting mirror 22 and a lens 34 and reaches a sensor 36, which is connected to an evaluation unit 37. The evaluation unit 37 detects the measured inspection radiation 33 and triggers the desired reactions in devices 38 connected at its output end as a function of the detected radiation 33. In the present case, the device 38 is a monitor, whose screen displays the quality of the weld seam 15 that has been produced in the workpiece 10.

If a weld seam 15 is present in the area of the workpiece 10 that is being covered, then, depending on the condition of the weld seam, the special conditions shown in FIG. 4 result. In front of the weld seam 15, the reflected radiation 32 and the exit radiation 33 described above remain the same relative to the angle of incidence of the inspection radiation 30, but after the weld seam 15, the reflected radiation 32' and exit radiation 33' deviate significantly. The rough interface 25 in the region of the weld seam 15, where diffuse scattering 32" occurs, contributes to this deviation.

This has the result that the area covered by the device 40 in FIG. 2 produces cumulative exit radiation 33' that differs significantly in FIG. 4 from that which is produced in the corresponding area without a weld seam in the workpiece 10 in FIG. 3. Multiple reflections occur in the transparent plastic 11 and possibly also in the area of the weld seam 15. The region of the exit radiation of interest 33' can be detected by adjusting the optics. This is accomplished by a sensor 36, whose output is connected to an evaluation unit 37. The measurement result is displayed on a display device 38. The use of the method of the invention showed that even small deviations from the reference value in the formation of the weld seam 15 can be clearly detected. Therefore, workpieces with weld seams 15 that are within tolerance can be clearly distinguished from those to be regarded as rejects.

The method described above can be used not only for workpieces 10 in which the weld seam is formed by laser radiation, but also in workpieces in which the weld seams are produced by any other desired method, e.g., friction welding or ultrasonic welding. Moreover, the method of the invention does not have to be used at the same time as the welding operation, because, in contrast to the state of the art, the thermal radiation emitted by the weld seam is not used for the measurement. As was explained above, this method uses inspection radiation 30 that is completely independent of the thermal radiation and can be used at any time. The inspection radiation 30 can also act from several sides on the workpiece 10. Consequently, it is also possible to use several radiation sources 31. This can be done, for example, with the additional method of the invention shown in FIG. 5.

Figure 5:
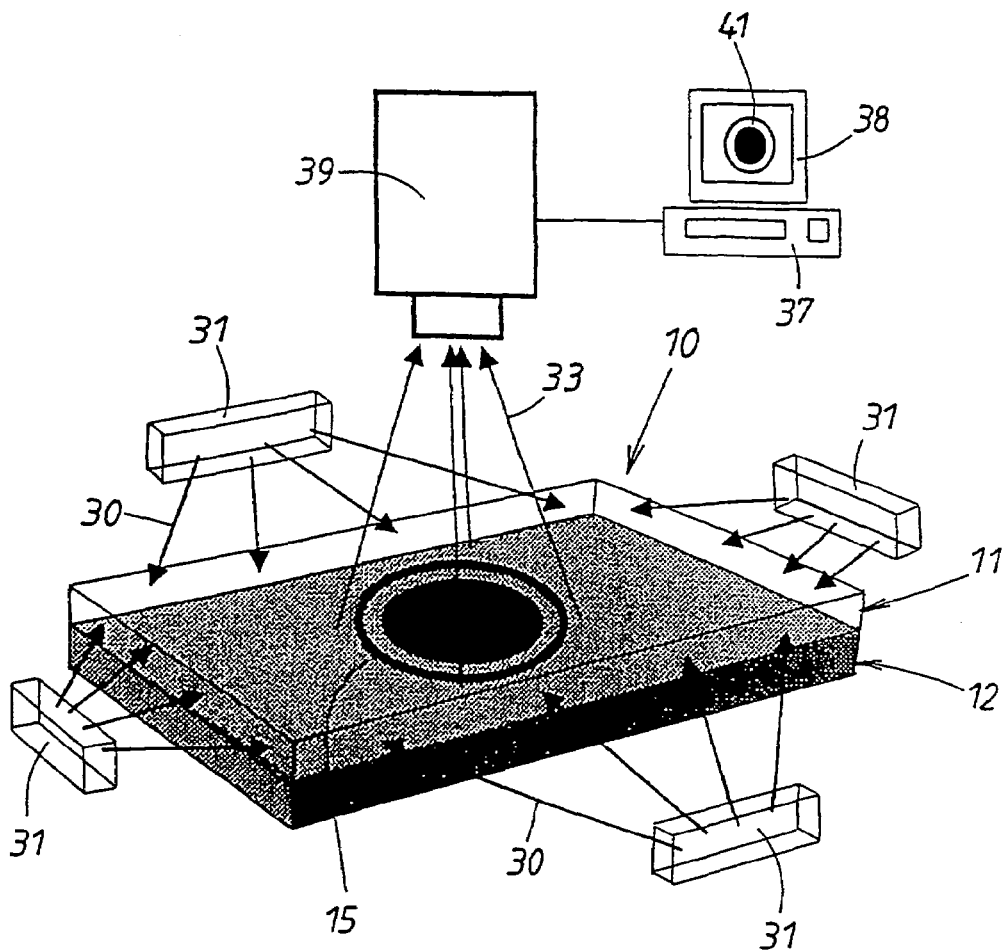
FIG. 5 shows another method of inspection in accordance with the invention for determining the quality of the weld seam.

In FIG. 5, analogous parts are indicated by the same reference numbers as in the preceding embodiment, and to this extent, the preceding description also applies here. It will only be necessary to describe the differences.

In FIG. 5, the workpiece 10 previously described in connection with FIG. 1 is being inspected with respect to the quality of the weld seam 15 produced in it. The inspection radiation 30 can act on the workpiece 10 from several sides. Therefore, as FIG. 5 illustrates, several radiation sources 31 can be used. In FIG. 5, the inspection radiation 30 is directed at the workpiece 10 from all sides. Depending on the quality of the weld seam 15, there are differences in the radiation 33 exiting the workpiece 10. In FIG. 5, this radiation 33 is detected by a CCD camera 39, which receives an image of the weld seam 15. The image is analyzed in the associated evaluation unit 37 by image-processing software. A suitably intensified and enlarged image 41 of the weld seam 15 previously produced in the workpiece 10 then appears on the display device 38. Depending on the result of the image 41, suitable reactions can then be carried out by monitoring personnel or by an automatic monitoring unit.

However, it is also possible to use as the inspection radiation 30 the laser radiation 20 itself, however, offset with respect to time from the welding process. In that case, the laser radiation 20 is once again moved along the path of the welding seam 15 after the welding procedure has been concluded. It is advantageous if the laser radiation 20 is raised to a lower power in order not to damage the workpiece 10 or the welding seam 15. Depending on the quality of the welding seam 15, the radiation 33 emanating from the workpiece 10 differs. Depending on the determined quality, appropriate reactions can be carried out by a control person or by an automated monitoring device.

Figure 7:
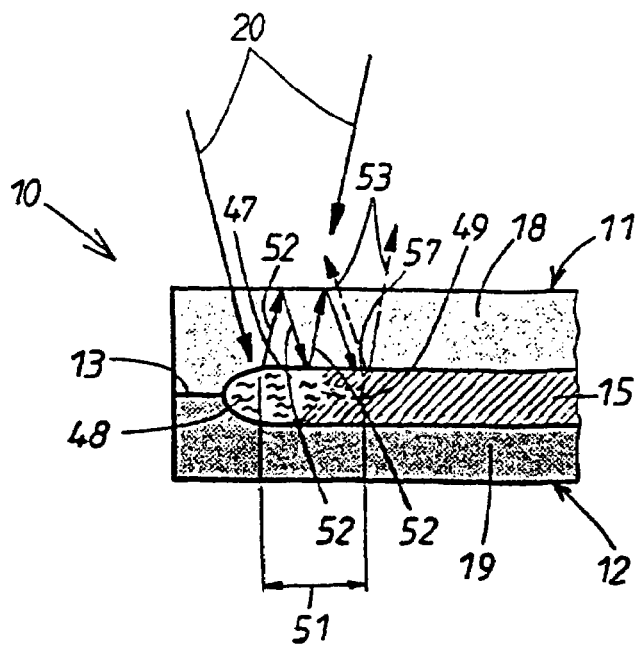
FIG. 7 shows an enlarged section of the workpiece indicated in FIG. 6, on the basis of which the special manner of operation of this method will be explained.
Figure 6:
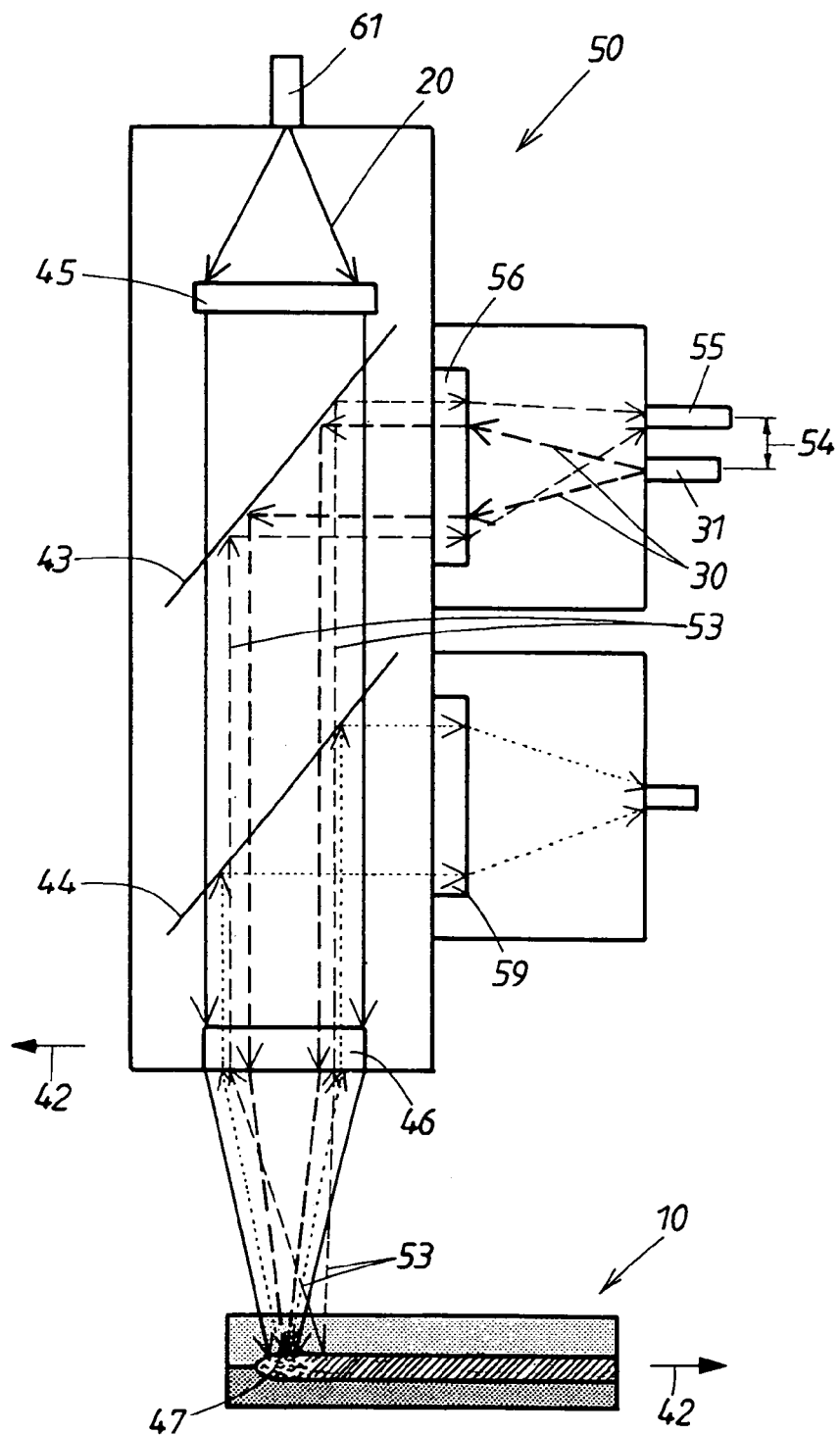
FIG. 6 shows a schematic longitudinal cross section through a device for another embodiment of the inspection method of the invention.

FIG. 6 shows a processing head 50, which can be moved relative to a workpiece 10 in the directions indicated by the two arrows 42. A semiconductor laser module not shown in FIG. 6 produces a laser beam 20, which enters the processing head 50 by an entrance 61, specifically, a beam waveguide, and is indicated by solid arrows in FIG. 6. The laser beam 20 is collimated by a lens 45, passes through two mirrors 43, 44 and is bundled by a collimator 46 and focused on a well-defined area at 47. As the enlargement in FIG. 7 shows, the focus 47 is then located on the contact surface 13 between the two plastic parts 11, 12 already described in connection with FIGS. 3 and 4, of which the upper part 11 is made of a plastic material 18 that is transparent or either slightly or strongly scattering. The critical factor is that the plastic part 12 consists of a plastic material 19 that absorbs the laser radiation 20. The wavelength of this laser radiation 20 can be about 800-940 nm.

A melt 48 of both materials 18, 19 forms in the area of the focus 47. During the movement 42 of the workpiece 10 relative to the processing head 50, the focus 47 moves along the workpiece, and the melt gradually undergoes solidification 49. The weld seam 15 forms in this way. At the same time, the laser light 20 in the interior of the transparent or slightly scattering material 18 of the first plastic part 11 is scattered in analogy to FIGS. 2 and 4. The scattered radiation is illustrated by solid arrows 52. By repeated reflections, the scattered radiation 52 also reaches a specific inspection point 57, which is located at a well-defined distance 51 from the focus 47. After repeated scattering 52, exit radiation 53 emerges, which is indicated by short-dash lines in FIGS. 6 and 7. The exit radiation 53 emerging from the inspection point 57 is detected by the optical component 46 and collimated. The exit radiation 53 passes through the lower mirror 44 but is reflected by the upper mirror 43 and finally reaches a detector 55. The detector 55 is offset 54 relative to a central axis that defines the optical beam path, but is not shown in the drawing. This offset 54 takes into account the above-mentioned distance 51 of the observed inspection point 57 from the melting point 48. The same process occurs at the detector that has already been described in connection with the first embodiment, following the sensor 36.

The processing head 50 also has a radiation source 31 for electromagnetic inspection radiation 30 that is independent of the laser light, and has a wavelength of, for example, 750-800 nm. This processing head 50 thus makes it possible, as an alternative to or in addition to the above-described inspection based on the exit radiation 53 of the welding beam 20, to perform an inspection that is independent of that method of inspection. This inspection can also be made by means of a detector 55 that detects the above-described inspection point 57 in the workpiece 10. An optical component 56 focuses and collimates the exit radiation 53 and the inspection radiation 30, respectively.

Finally, a pyrometer 58 is also integrated in the processing head 50. The pyrometer 58 detects the thermal radiation, which is indicated in FIG. 6 by dotted arrows 60, after the thermal radiation passes through an optical component 59. The thermal radiation 60 is emitted by the weld. This is used to regulate the melt temperature. At the same time, the welding result can be inspected by the inspection radiation 30, whose exit radiation 33, 33' from the inspection point 57 is detected by the detector 55. The processing head 50 can thus cover all three of the methods described above for inspecting the resulting weld seam 15 or weld 47. These measurement results are then analyzed either together or separately in connected devices.

The pyrometer 58 can be integrated with the source of the laser light 20 in a feedback control system. The thermal radiation emitted by the weld 47 is detected by the pyrometer 58 and analyzed in the connected devices. In the event of deviations from a desired reference value, the result of the analysis is used to regulate the intensity of the laser light 20.

The above-described components integrated in the processing head 50 may also be housed in individual units. These individual units are then placed together to form groups of units.

The invention claimed is:

1. A method for inspecting a weld seam between two plastic parts of a workpiece made of weldable material, the method comprising producing the weld seam by using a laser beam,
wherein one of the plastic parts of the workpiece is essentially transparent to laser radiation and the other plastic part absorbs the laser radiation,
determining the quality of the weld seam produced in this way by optical means; the method further comprising
after producing the weld seam by laser radiation, directing an electromagnetic control radiation against the weld seam;
wherein one of the two plastic parts is also transparent to the control radiation,
introducing the control radiation into the interior of the transparent plastic part such that the control radiation impacts the welding seam which has already solidified,
wherein the control radiation is reflected at a contact surface between the plastic parts and at an interface of the weld seam and is partly transmitted back out of the workpiece;
during the measurement of the exiting radiation, measuring only the reflected radiation emanating from an already solidified location of the weld seam and supplying the reflected radiation to an evaluation unit;
conducting the control radiation emanating from the workpiece on its path to the measuring location partially along optical elements along which the laser light is also conducted in an opposite direction to the welding point in the workpiece;

and, using the evaluation unit, detecting a disturbance of the measured exiting radiation caused by an imperfect weld and a reaction triggering a reaction in a monitoring device by the disturbance of the measured exiting radiation.

2. The method according to claim 1, comprising using additional radiation that is independent of the laser radiation as the control radiation.

3. The method according to claim 1, wherein the control radiation is emitted by the same source that produces the laser beam used for producing the weld seam.

4. The method according to claim 3, wherein the measured exit radiation is the laser radiation scattered in the workpiece, wherein the exit radiation emanates from a location which is spatially distant from a focus of the laser beam where the liquid melt is currently located.

5. The method according to claim 1, comprising conducting the direction of incidence of the control radiation on the workpiece at an angle with the direction of incidence of the laser beam.

6. The method according to claim 1, comprising conducting the direction of incidence of the control radiation on the workpiece coaxially with the direction of incidence of the laser beam.

7. The method according to claim 1, comprising initially completely welding the workpiece and placing the welded product underneath a CCD camera, illuminating the welded product located under the CCD camera using the control radiation, and analyzing the image of the welded product protected by the CCD camera using image-processing software in the evaluation unit connected to an output of the camera.

* * * * *